United States Patent
Kornet et al.

(10) Patent No.: US 8,504,161 B1
(45) Date of Patent: Aug. 6, 2013

(54) MODULATE VAGAL SIGNALS TO REDUCE INFLAMMATION

(75) Inventors: Lilian Kornet, Maastricht (NL); Sergio Valsecchi, Rome (IT)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/568,281

(22) Filed: Aug. 7, 2012

(51) Int. Cl.
*A61N 1/36* (2006.01)

(52) U.S. Cl.
USPC .................................. 607/50; 607/2; 607/118

(58) Field of Classification Search
USPC ........ 607/1, 2, 9, 14, 17, 45, 50, 62, 117–118
See application file for complete search history.

(56) References Cited

U.S. PATENT DOCUMENTS

| | | | | |
|---|---|---|---|---|
| 5,700,282 | A * | 12/1997 | Zabara | 607/9 |
| 6,341,236 | B1 * | 1/2002 | Osorio et al. | 607/45 |
| 6,610,713 | B2 | 8/2003 | Tracey | |
| 6,718,208 | B2 | 4/2004 | Hill | |
| 6,838,471 | B2 | 1/2005 | Tracey | |
| 7,711,430 | B2 | 5/2010 | Errico et al. | |
| 7,715,915 | B1 * | 5/2010 | Ryu et al. | 607/9 |
| 7,908,008 | B2 | 3/2011 | Ben-David et al. | |
| 8,036,745 | B2 | 10/2011 | Ben-David et al. | |
| 2003/0144709 | A1 * | 7/2003 | Zabara et al. | 607/46 |
| 2005/0065553 | A1 | 3/2005 | Ben Ezra et al. | |
| 2006/0178703 | A1 | 8/2006 | Huston | |
| 2007/0093870 | A1 * | 4/2007 | Maschino | 607/2 |
| 2007/0276443 | A1 | 11/2007 | Shafer | |
| 2008/0086182 | A1 | 4/2008 | Ben-David et al. | |
| 2008/0161894 | A1 * | 7/2008 | Ben-David et al. | 607/116 |
| 2009/0082823 | A1 * | 3/2009 | Shuros et al. | 607/17 |
| 2009/0247934 | A1 | 10/2009 | Tracey | |
| 2009/0254143 | A1 * | 10/2009 | Tweden et al. | 607/40 |
| 2010/0069985 | A1 * | 3/2010 | Stahmann | 607/9 |
| 2011/0015695 | A1 | 1/2011 | Pasricha | |
| 2011/0054569 | A1 | 3/2011 | Zitnik | |
| 2011/0106208 | A1 | 5/2011 | Faltys | |
| 2011/0319958 | A1 * | 12/2011 | Simon et al. | 607/42 |
| 2012/0330373 | A1 * | 12/2012 | Ternes et al. | 607/42 |
| 2013/0079745 | A1 * | 3/2013 | Thornton et al. | 604/500 |

FOREIGN PATENT DOCUMENTS

WO 2006/073484 A2 7/2006

OTHER PUBLICATIONS

Borovikova, L. V. et al. Vagus nerve stimulation attenuates the systemic inflammatory response to endotoxin. Nature 405, 458-462 (2000).
Bernik, T. R. et al. Pharmacological stimulation of the cholinergic antiinflammatory pathway. J. Exp. Med. 195, 781-788 (2002).

(Continued)

*Primary Examiner* — Niketa Patel
*Assistant Examiner* — Christopher A Flory
(74) *Attorney, Agent, or Firm* — Michael C. Soldner

(57) ABSTRACT

A medical device is configured to perform a method for modulating vagal nerve signals to reduce inflammation. A sensing module of the medical device is enabled to receive an electrical signal from selected electrodes electrically coupled to the medical device. A controller coupled to the sensing module is configured to determine an inflammation metric from the sensed electrical signal. The metric is compared to an inflammation detection threshold. A pulse generator is controlled to selectively deliver electrical stimulation pulses via the plurality of electrodes in response to the metric meeting the inflammation detection threshold to modulate vagal nerve signals to cause an anti-inflammatory response.

21 Claims, 7 Drawing Sheets

OTHER PUBLICATIONS

Constantini, T.W., et al., "Efferent vagal nerve stimulation attenuates gut barrier injury after burn: modulation of intestinal occludin expression" J Trauma. Jun. 2010;68(6):1349-54; discussion 1354-6.

Henningsen, K.M., et al., "Prognostic impact of hs-CRP and IL-6 in patients with persistent atrial fibrillation treated with electrical cardioversion" Scand J Clin Lab Invest. 2009;69(3):425-32.

Pavlov, V.A., et al. "The Cholinergic Anti-inflammatory Pathway: A Missing Link in Neuroimmunomodulation", Molecular Medicine, May-Aug. 2003, vol. 9(5-8), pp. 125-134.

Pavlov, V.A., et al. "Brain acetylcholinesterase activity controls systemic cytokinase through the cholinergic anti-inflammatory pathway" Brain Behavior, and Immunity, 2009, vol. 2, pp. 41-45.

Sloan RP, et al., "RR Interval Variability is inversely related to inflammatory markers: The CARDIA Study". Mol Med 13(304) 178-184, Mar.-Apr. 2007.

Van Der Zanden, EP, et al. "Vagus nerve activity augments intestinal macrophage phagocytosis via nicotinic acetylcholine receptor alpha4beta2" Gastroenterology. Sep. 2009;137(3):1029-39, 1039. e1-4. Epub May 7, 2009.

Bettoni, M., et al. "Autonomic tone variations before the onset of paroxysmal atrial fibrillation" Circulation, Jun. 11, 2002, vol. 105, pp. 2753-2759.

Tracey, KJ. "The inflammatory reflex". Nature vol. 420, Dec. 2002, pp. 853-859.

* cited by examiner

MODULATE VAGAL SIGNALS TO REDUCE INFLAMMATION

FIELD OF THE DISCLOSURE

The present disclosure relates generally to medical devices and, in particular, to an apparatus and method for modulating vagal nerve signals to reduce inflammation.

BACKGROUND

An exaggerated inflammatory response can occur after surgery or trauma, which can lead to sepsis and septic shock. The number of diseases being classified as inflammatory types of diseases associated with long-term, systemic inflammation is on the rise. Examples include diabetes, atherosclerosis, heart failure, myocardial infarct, and auto-immune diseases like Graves' disease, colitis, Crohn's disease, and many more. Uncontrolled inflammation can lead to critical acute states following surgery or trauma or chronic disease states due to long-term inflammatory conditions. Electrical stimulation of the vagal nerve can attenuate inflammation through activation of nicotinic acetylcholine receptors. Activation of this so-called "cholinergic anti-inflammatory pathway" can provide an anti-inflammatory response, potentially beneficial in controlling acute inflammation, e.g. following surgery or trauma, as well potentially managing chronic inflammatory types of diseases.

DETAILED DESCRIPTION

Figure 1:
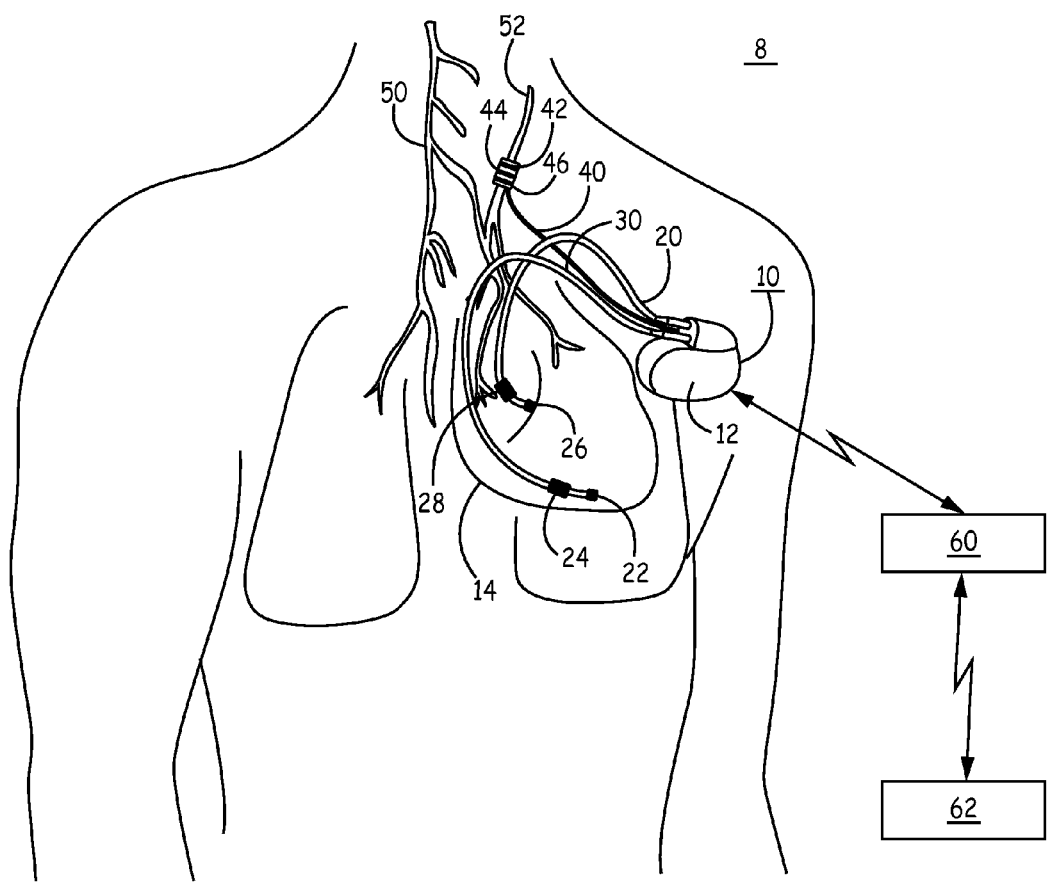
FIG. 1 is a schematic diagram of one embodiment of an implantable medical device system that may be used for modulating vagal nerve signals to reduce inflammation.

FIG. 1 is a schematic diagram of one embodiment of an implantable medical device system 8 that may be used for modulating vagal nerve signals to reduce inflammation. System 8 includes an implantable medical device 10, cardiac leads 20 and 30, a nerve lead 40, and an external programmer 60. External programmer 60 may be in operative communication with a remote patient management database 62, such as Carelink®, available from Medtronic, Inc., Minneapolis, Minn.

In the illustrative embodiment, IMD 10 is coupled to the patient's heart 14 via leads 20 and 30. Right atrial (RA) lead 20 is a transvenous lead shown extending into the patient's right atrium and carrying sensing electrodes 26 and 28. Right ventricular (RV) lead 30 is shown as a transvenous intracardiac lead extending into the right ventricle and carrying sensing electrodes 22 and 24. Electrodes 22, 24, 26 and 28 are used for sensing cardiac signals, which may include cardiac electromyogram (EGM) signals attendant to the depolarization of the myocardial cells and/or cardiac neural signals. In one embodiment, cardiac P-waves arising from the right atrial (RA) chamber of the patient's heart 14 and/or R-waves arising from the right ventricular (RV) chamber are sensed using respective RA lead 20 and RV lead 30. Sensed cardiac events or EGM signal features, e.g. P-waves, R-waves, and S-T segments, may be used for determining a metric of inflammation in some embodiments.

Additionally or alternatively, cardiac leads 20 and 30 may be adapted to be positioned along cardiac neural tissue for sensing cardiac nerve signals using electrodes 22, 24, 26 and 28. As will be described herein, aspects of a vagal nerve signal such as signals carried by a cardiac nerve or plexus may be measured to determine a metric of inflammation.

RV electrodes 22 and 24 and RA electrodes 26 and 28 may additionally be used for delivering pacing pulses to the right ventricle and/or right atrium, respectively, of the patient's heart 14 when IMD 10 is configured to deliver bradycardia pacing, cardiac resynchronization therapy, or other pacing therapies. Leads 20 and 30 and associated electrodes 22, 24, 26 and 28 may additionally or alternatively be adapted for delivering electrical stimulation pulses to cardiac fat pads for stimulating cardiac neural tissue to modulate vagal signals for inducing an anti-inflammatory response.

In other embodiments, IMD 10 may be coupled to one or more cardiac leads embodied as epicardial leads carrying electrodes for sensing cardiac signals (myocardial or neural signals) and/or for delivering electrical stimulation pulses. For example, an epicardial lead may be used to deliver electrical stimulation therapy to an epicardial fat pad to stimulate cardiac nerve branches or plexuses for modulating vagal nerve signals and inducing an anti-inflammatory response.

IMD 10 is shown coupled to a nerve lead 40. In some embodiments, a nerve lead carrying electrodes 42, 44 and 46, e.g. mounted along a nerve cuff, is adapted for positioning along a vagus nerve or one of its branches, plexuses or ganglion. Electrodes 42, 44 and 46 may be used for sensing vagal nerve signals for use in detecting inflammation and/or delivering vagal nerve electrical stimulation pulses to induce an anti-inflammatory response. In a tripolar arrangement as shown, a first bipole pair selected from electrodes 42, 44 and 46 may be used for sensing vagal nerve signals and a second, different bipole pair selected from electrodes 42, 44 and 46 may be used for delivering electrical stimulation pulses. As will be described herein, electrical stimulation pulses may be delivered for inducing an indirect compound action potential signal. Aspects of the compound action potential signal may then be measured for determining an inflammation metric. Additionally or alternatively, therapeutic electrical stimulation pulses may be delivered using the nerve electrodes 42, 44 and 46 for controlling inflammation.

Nerve lead 40 is shown as a tripolar lead, however in other embodiments a nerve lead used in a system for detecting inflammation and modulating vagal signals for inducing an anti-inflammatory response may be provided as a bipolar lead or a multi-polar lead carrying multiple electrodes selectable in any combination. One or more nerve leads may be provided in various embodiments and may replace or be used in conjunction with cardiac leads 20 and 30.

As will be further described herein, an electrical signal is received by IMD 10 via selected ones of the lead(s) and electrodes coupled to IMD 10 and used for automatically detecting a pro-inflammatory condition. Upon detecting a pro-inflammatory condition, IMD 10 delivers electrical stimulation pulses to the right vagus nerve 50, left vagus nerve 52, or a vagus nerve branch or plexus to modulate vagal nerve signals to induce an anti-inflammatory response. The electrical signal received by IMD 10 and used for automatically detecting a pro-inflammatory condition may be received from a cardiac lead, such as lead 20 or 30, or from a nerve lead, such as nerve lead 40. Stimulation pulses delivered to induce an anti-inflammatory response may be delivered via a nerve lead, such as lead 40, or a cardiac lead, such as RA lead 20 or RV lead 30.

Among the potential stimulation sites that can be selected for delivering an anti-inflammatory stimulation therapy are the right vagus nerve, the left vagus nerve, and any branch of the right or left vagus nerves such as, but not limited to, the cardiac branches, an atrial or ventricular fat pad approached endocardially or epicardially, laryngeal branches, gastric branches, splenic branches, pancreatic branches, pyloric branches, branches to small and large intestines, esophageal branches, and pulmonary branches. Numerous lead and electrode configurations are possible for using the techniques described herein. The lead and electrode configuration used in an implantable system using the presently disclosed techniques will be selected based on ease of use and access to a targeted sensing or stimulation site along the vagal nerve tree. As used herein, the sensing or stimulation of a "vagal nerve" refers to sensing a nerve signal or delivering stimulation pulses at any location along the vagal nerve tree, including the right vagus nerve, the left vagus nerve, or any branch, plexus or ganglion of the right and left vagus nerves.

IMD circuitry configured for performing the methods described herein and associated battery(ies) are housed within a sealed housing 12. Housing 12 may be conductive so as to serve as an electrode for use as an indifferent electrode during sensing. As such, housing 12 is also referred to herein as "housing electrode" 12.

Sensed electrical signals and therapy delivery data acquired by IMD 10 can be transmitted to external programmer 30. External programmer 30 is used, e.g. in a clinic or hospital, to communicate with IMD 10 via wireless telemetry for retrieving data from IMD 10. Programmer 30 is used to program commands or operating parameters or programs into IMD 10 for controlling IMD functions and to interrogate IMD 10 to retrieve data, including device operational data as well as physiological data accumulated in IMD memory. Examples of communication techniques that may be used by IMD 10 and programmer 30 include low frequency or radiofrequency (RF) telemetry, which may be an RF link established via Bluetooth, WiFi, or MICS. In alternative embodiments, programmer 60 may be embodied as an external device used by the patient, such as a home monitor or a hand held device. In such embodiments, programmer 60 may be used to retrieve data from IMD 10 for transmission to remote database 62 and, in response, receive operating or programming commands from database 62 for programming into IMD 10.

In some embodiments, a user, either a patient or clinician, may manually enter data into remote database 62 or programmer 60 that is then used by system 8 to control electrical stimulation therapy delivered to a vagal nerve. For example, a pro-inflammatory marker may be measured in blood or urine from the patient. The blood- or urine-based pro-inflammatory marker measurement may then be entered into remote database 62 or programmer 60 for use in charting a patient's pro-inflammatory response and monitoring effectiveness of a vagal stimulation therapy. The marker measurement may be transmitted to IMD 10 via telemetry and used by control circuitry in IMD 10 to automatically adjust the vagal stimulation therapy. Among the biomarkers of a pro-inflammatory response that may be measured are interleukin 6 (IL-6), tumor necrosis factor (TNF) alpha, C-reactive protein (CRP), white blood cell count, albumin, and plasma norepinephrine.

Figure 2A:
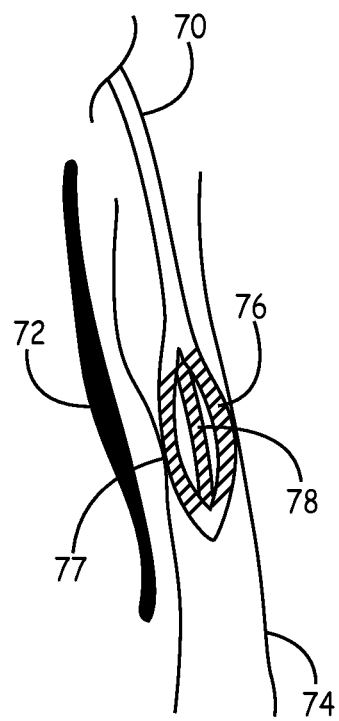
FIG. 2A is a schematic illustration of an alternative embodiment of a nerve lead used for stimulating a vagal nerve for inducing an anti-inflammatory response.

FIG. 2A is a schematic illustration of an alternative embodiment of a nerve lead 70 used for stimulating a vagal nerve 72 for inducing an anti-inflammatory response. It is contemplated that a nerve lead coupled to IMD 10 may be embodied as an extravenous lead tunneled to or positioned alongside a vagal nerve as shown in FIG. 1, or as an intravenous lead as shown in FIG. 2A.

Lead 70 in FIG. 2A is advanced along a blood vessel 74 to operatively position electrodes 76, 77 and 78 adjacent nerve 72 for sensing nerve fiber signals and/or delivering anti-inflammatory stimulation pulses to nerve 72. In the illustrative embodiment shown, the electrodes 76, 77 and 78 are shown configured as "arms" of a "basket" electrode. Each of electrodes 76, 77 and 78 may be coupled to respective insulated electrical conductors extending within the elongated body of lead 70. A bipolar or tripolar combination of electrodes 76, 77 and 78 may be used for sensing and/or for stimulating nerve 72. Electrodes 76, 77, and 78 are depicted as coil electrodes extending along a basket-shaped portion of the lead body.

In alternative embodiments, a transvenous lead or catheter that remains within a blood vessel for stimulating an adjacent vagal nerve may carry a spiral electrode, ring electrode, helical electrode, or any other type of electrode appropriately sized for advancement along a blood vessel in proximity to a vagal nerve. An intravascular lead may include fixation members for maintaining the electrodes 76, 77 and 78 at a desired location along a blood vessel. The intravascular lead electrodes themselves may provide fixation or anchoring in some embodiments, such as a helical electrode which may be anchored into a vessel wall or the basket-type configuration shown which may press against the intraluminal walls of the vessel.

Figure 2B:
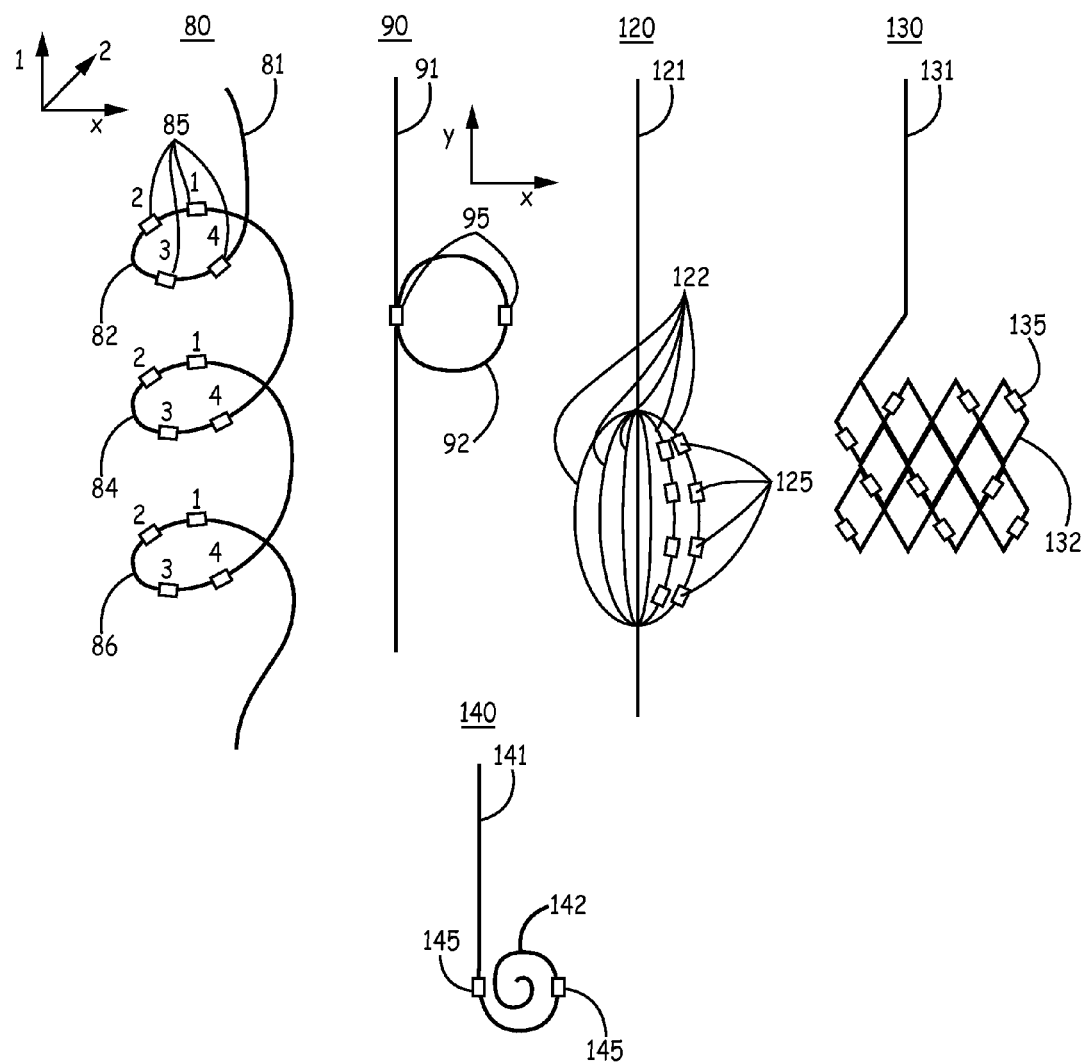
FIG. 2B is an illustration of several different intravenous lead configurations that could be used for sensing vagal nerve signals and/or stimulating a vagal nerve.

FIG. 2B is an illustration of several different intravascular lead configurations that could be used for sensing vagal nerve signals and/or stimulating a vagal nerve. Lead 80 includes an elongated lead body 81 including one or more pre-formed coils 82, 84 and 86. Along each coil, one or more electrode(s) 85 are positioned which may be selected in any combination for sensing a vagal nerve signal and/or delivering vagal nerve stimulation pulses. The coils 82, 84 and 86 are shown to be non-planar with the non-coiled, substantially straight portion of the lead body 81. For example, coils 82, 84, and 86 may be pre-formed to be substantially perpendicular to a plane of the lead body 81. The electrodes 85 may each be coupled to respective insulated conductors extending through lead body 81 such that each coil 82, 84, and 86 provides multiple, individually selectable poles. Alternatively electrodes 85 on a given coil 82 may be coupled to a common conductor such that each coil 82, 84, and 86 forms an individually selectable pole.

Lead 90 in FIG. 2B is provided with an elongated lead body 91 having one or more pre-formed loops 92, each carrying one or more electrodes 95. In the example shown, a single loop 92 carrying bipolar electrode pair 95 can be used for sensing nerve signals and/or stimulating a vagal nerve extending adjacent a blood vessel through which lead 90 is advanced. In contrast to the coils 82, 84, and 86 of lead body 81, the loop(s) 92 of lead body 91 are shown to be substantially co-planar with a plane of the lead body 91.

Lead 120 is provided having a lead body 121 carrying a basket type electrode configuration having multiple "arms" 92 each carrying multiple electrodes 95. As such each lead body arm 92 provides multiple individually selectable poles that may be selected in any combination for establishing a sensing and/or stimulation vector.

Lead 130 includes a lead body 131 enclosing insulated electrical conductors extending to and coupled to multiple electrodes 135 arranged along a stent structure 132, which may be an expandable stent, for positioning electrodes 135 against the inner wall of a vascular lumen. The electrodes 135 may each be coupled to respective insulated conductors extending through lead body 131 and stent 132 may be non-conductive to enable sensing and/or stimulation vector selection using electrodes 135 in any combination.

Lead 140 is another example of an intravenous lead that may be used for stimulating a vagal nerve or sensing vagal nerve signals. Lead 140 includes a lead body 141 having a pre-formed "pig-tail" 142 shaped at a distal lead end. The "pig-tail" 142, i.e. the spirally shaped distal lead portion, carries two or more electrodes 145 that may be selected in any combination for establishing a sensing or stimulation electrode vector.

The illustrative embodiments described herein pertain primarily to an implantable device system for delivering an anti-inflammatory therapy, however, it is contemplated that a medical device and associated leads and electrodes that detect a pro-inflammatory response and deliver anti-inflammatory stimulation therapy may be wholly implantable, include some implanted components and some external components, or be wholly external. For example, ECG electrodes may be attached to a patient's skin for sensing cardiac signals received by a control unit for detecting a pro-inflammatory response. Surface electrodes, electrically coupled to an external pulse generator, may be attached to a patient in a location that enables electrical stimulation of a vagal nerve, for example along a patient's neck. The control unit would control the external pulse generator to deliver anti-inflammatory stimulation therapy in response to detecting the pro-inflammatory response.

Figure 3:
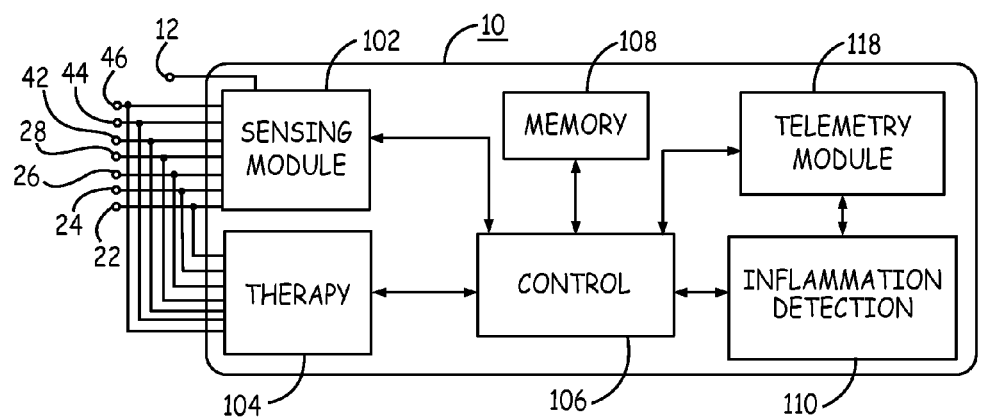
FIG. 3 is a functional block diagram of the medical device shown in FIG. 1 according to one embodiment.

FIG. 3 is a functional block diagram of IMD 10 according to one embodiment. IMD 10 includes a sensing module 102, a therapy delivery module 104, a control unit 106 and associated memory 108, an inflammation detection module 110, and telemetry module 118. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Sensing module 102 receives electrical signals from sensing electrodes coupled to IMD 10, e.g. any of electrodes 22, 24, 26, 28, 42, 44, and 46 carried by leads 20, 30 or 40 and housing electrode 12. As described above, cardiac electrodes 22, 24, 26 and 28 (and housing electrode 12) may be used to sense signals attendant to the depolarization and repolarization of myocardial tissue, e.g. P-waves, R-waves, and T-waves, for use in determining a pro-inflammatory metric related to the heart rhythm. Cardiac electrodes 22, 24, 26, and 28 may alternatively be used to sense nerve signals intracardially from a cardiac nerve or plexus by positioning the corresponding tip of lead 20 or 30 at a location of cardiac nerve tissue, such as the parasympathetic nerves innervating the atrioventricular (AV) node or sinus node. Nerve lead electrodes 42, 44 and 46 may additionally or alternatively be used to sense vagal nerve signals for use in determining a pro-inflammatory metric.

Sensing module 102 may include a switch module for selectively coupling electrodes 22, 24, 26, 28, 42, 44, 46 and housing electrode 12 to sensing module 102 in order to monitor myocardial and/or neural electrical activity of heart 14 and/or a vagal nerve. The switch module may include a switch array, switch matrix, multiplexer, or any other type of switching device suitable to selectively couple electrodes to sensing module 102. In some examples, control unit 106 selects the electrodes to function as sense electrodes, or the sensing vector, via the switch module within sensing module 102.

Sensing module 102 may include multiple sensing channels, each of which may be selectively coupled to respective combinations of electrodes 22, 24, 26, 28, 42, 44, 46 and housing 12 to detect electrical activity of a particular chamber of heart 14 or vagal nerve, e.g. an atrial EGM sensing channel and a ventricular EGM signal channel, and/or one or more vagal nerve signal channels. While a particular lead and electrode configuration is shown in conjunction with IMD 10 in FIG. 1, it is contemplated that numerous electrode and lead configurations are possible which may include electrodes positioned along more than one vagal nerve. Accordingly, sensing module 102 may be configured with multiple nerve sensing channels for sensing electrical signals from the right vagus nerve, the left vagus nerve and/or any branches or plexuses of the right or left vagus nerves.

Each sensing channel may comprise a sense amplifier that outputs an indication to control unit 106 of a sensed event. For example, a sense amplifier output may be produced in response to sensing of a myocardial event signal, e.g. P-wave, or R-wave, in a respective chamber of heart 14. In this manner, control unit 106 may receive sense event signals corresponding to the occurrence of sensed R-waves and P-waves in the respective chambers of heart 14. Sensing module 102 may further include digital signal processing circuitry for providing control unit 106 and/or inflammation detection module 110 with digitized EGM and/or nerve signals, which may be used for determining an inflammation metric. Inflammation detection module 110 may receive analog and/or digitized signals from sensing module 102 for use in detecting inflammation.

Memory 108 may include computer-readable instructions that, when executed by control unit 106 and inflammation detection module 110, cause IMD 10 to perform various functions attributed throughout this disclosure to IMD 10, control module 106 and inflammation detection module 110. The computer-readable instructions may be encoded within memory 108. Memory 108 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Control unit 106 may include any one or more of a microprocessor, a controller, a digital signal processor (DSP), an application specific integrated circuit (ASIC), a field-programmable gate array (FPGA), or equivalent discrete or integrated logic circuitry or state machine. In some examples, control unit 106 may include multiple components, such as any combination of one or more microprocessors, one or more controllers, one or more DSPs, one or more ASICs, or one or more FPGAs, as well as other discrete or integrated logic circuitry or state machines. The functions attributed to control unit 106 herein may be embodied as software, firmware, hardware or any combination thereof. Inflammation detection module 110 may be implemented as a portion of control unit 106. In one example, inflammation detection module 110 may, at least in part, be stored or encoded as instructions in memory 108 that are executed by control unit 106.

Control unit 106 includes a therapy control unit that controls therapy delivery module 104 to deliver electrical stimulation therapy to a vagal nerve according to a selected stimulation pattern, which may be stored in memory 108. Control unit 106 and inflammation detection module 110 operate to determine an inflammation metric, detect an inflammatory response or a rising inflammatory response based on the inflammation metric, and control an electrical stimulation therapy delivered to induce a neurally-triggered anti-inflammatory response. One or more inflammation metrics are determined from the signal(s) received from sensing module 102. The inflammatory response is detected by comparing the metric(s) to previously established threshold or other detection criteria, which may be based on a baseline measurement of the metric(s) or clinical data.

Upon detecting an inflammatory response (or a rising or worsening trend of an inflammatory response), control unit 106 controls therapy delivery module 104 to deliver the anti-inflammatory therapy. Therapy delivery module 104 is electrically coupled to electrodes 22, 24, 26, 28, 42, 44, 46 and housing electrode 12 (all of which are shown in FIG. 1). Therapy delivery module 104 includes an electrical pulse generator and is configured to generate and deliver electrical stimulation pulses to the vagal nerve system via selected combinations of electrodes 22, 24, 26, 28, 42, 44, 46 and housing electrode 12. The stimulation pulses are delivered according to a stimulation protocol stored in memory 108.

Memory 108 stores intervals, counters, and other data used by control unit 106 to detect an inflammatory condition and to control the delivery of electrical stimulation pulses by therapy delivery module 104. For example, memory 108 may store a stimulation burst pattern defining the frequency and number of pulses in a pulse train, the time intervals between pulse trains, the pulse amplitudes and pulse widths or other stimulation pattern control parameters. As will be described below, specific stimulation patterns may be established for selectively stimulating vagal nerve fibers, e.g. afferent vagal nerve fibers associated with a particular receptor or sensor of a given organ innervated by a vagal nerve.

Control unit 106 may respond to detection of inflammation by generating a patient or clinician alert, which may be transmitted by telemetry module 118. Control unit 106 may additionally respond to a worsening or improving inflammatory condition by adjusting the stimulation therapy being delivered by therapy delivery module 104. Adjustments may include increasing or decreasing a period of time therapy is delivered, increasing or decreasing the number of stimulation sites at which therapy is being delivered, altering a stimulation pulse amplitude or a control parameter affecting the stimulation pattern (e.g. frequency of pulses, number of pulses in a pulse train, duration of pulse trains, and intervals between pulse trains), or starting or stopping the stimulation therapy.

Telemetry module 118 is used to communicate with external programmer 60, for transmitting data accumulated by IMD 10 and for receiving interrogation and programming commands from external device 60. Under the control of control unit 106, telemetry module 118 transmits an alert to notify a clinician and/or the patient that IMD 10 has detected an inflammatory condition. This alert enables the clinician to increase monitoring of the patient and provide additional treatment as warranted.

Figure 4:
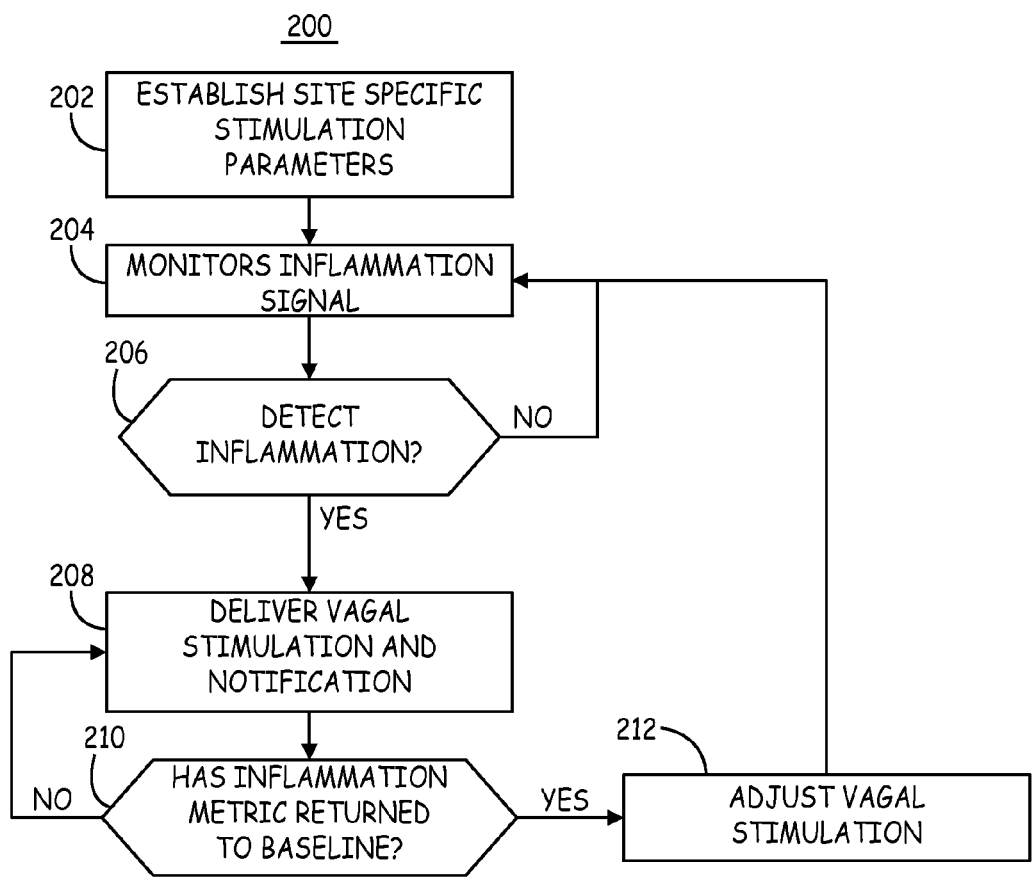
FIG. 4 is a flow chart of a method for treating an inflammatory condition according to one embodiment.

FIG. 4 is a flow chart of a method 200 for treating an inflammatory condition according to one embodiment. At block 202, stimulation parameters for a selected therapy delivery site are established. One or more stimulation sites may be selected for targeting either afferent or efferent nerve fibers or both. The stimulation parameters defined for delivering therapy at a selected site may include, but are not limited to, stimulation pulse amplitude, pulse width, pulse shape, pulse frequency, pulse train duration, and inter-pulse train interval. Nerve fibers in the vagal nerve have varying diameters, varying depolarization threshold amplitudes and frequencies, and varying conduction velocities unique to a particular nerve fiber. The varying nerve fibers each transfer particular information to or from the brain. Accordingly, a specific set of stimulation parameters may be established at block 202 for targeting modulation of signals along a particular nerve fiber by selecting stimulation parameters corresponding to a particular property of the intrinsic nerve fiber signals.

Various organs innervated by a vagus nerve branch send afferent signals to the brain via a nerve fiber modulated by a specific frequency pattern. For example, the lungs may send signals back to the brain at a frequency correlated to respiration rate. The heart may send signals to the brain at a frequency corresponding to a cardiac frequency. Additionally, an afferent nerve fiber may carry signals to the brain received from a particular physiological sensor or receptor, such as a stretch receptor or a chemoreceptor. For example, in the heart, ischemic receptors or chemical receptors might produce feedback signals to the brain to influence inflammation. The burst pattern and amplitude of an afferent nerve signal per cardiac cycle, for example, may depend on the type of receptor and therefore the vagal nerve fiber(s) influenced. Electrical stimulation using stimulation parameters selected to correspond to a property of a particular intrinsic afferent nerve signal may be used to artificially increase a feedback signal associated with inflammation.

Accordingly, specific stimulation parameters may be established at block 202 to stimulate afferent nerve fibers in a vagal nerve in some examples. The artificially increased, fiber-selective signals transmitted to the brain along the vagal tree will simulate increased inflammatory response signals. These "simulated inflammatory response" signals will trigger the brain to transmit efferent vagal signals to inflammation control centers, such as liver, spleen and intestines, that then cause an anti-inflammatory response to counteract the detected inflammation.

Site specific stimulation parameters may be defined at block 202 which modulate afferent signals along the vagal nerve system and block efferent transmission of stimulation pulses delivered to the stimulation site. For example, anodal blocking stimulation, depolarizing pre-pulses, slowly rising pulses, quasi-trapezoidal pulses, or other stimulation techniques may be used to block efferent transmission of electrical stimulation pulses and promote afferent transmission of the electrical stimulation therapy. When the stimulated afferent fibers transmit modulated nerve signals to the brain to simulate an increased inflammatory response, the brain will control efferent nerve fiber signals transmitted "downstream" to induce an anti-inflammatory response.

Additionally or alternatively, site specific stimulation parameters may be established for stimulating efferent nerve branches. For example, efferent nerve branches which transmit to the intestines, spleen and liver, which are involved in regulation of inflammation, may be stimulated.

At block 204, electrical signals received by sensing module 102 are monitored to enable the control module 106 to monitor an inflammation signal or metric. The inflammation metric is monitored by control module 106 by receiving an electrical signal sensed by sensing module 102, computing an inflammation metric from the signal, and comparing the metric to a threshold at decision block 206 for detecting an inflammatory condition.

In some embodiments, myocardial signals are monitored for detecting inflammation. The atrial rate, the relationship between the atrial and ventricular rates, and/or RR variability may be measured from sensed cardiac EGM signals to determine an inflammation metric at block 204 for example. Atrial fibrillation is one marker of a pro-inflammatory response. RR variability is inversely correlated to inflammatory markers. Elevation or depression of the S-T segment of an EGM or ECG signal is an indicator of myocardial ischemia which may also be associated with an inflammatory response. Accordingly, a cardiac EGM (or ECG) signal, i.e. a myocardial signal, may be an electrical signal sensed at block 204 for determining an inflammation metric.

Additionally or alternatively, a nerve signal, sensed from cardiac electrodes positioned along cardiac nerve tissue or nerve electrodes positioned along a vagal nerve, may be sensed by sensing module 102 for determining an inflammation metric at block 204. Afferent nerve fiber signals coming from a specific organ innervated by a vagus nerve branch can be identified by characteristic frequency components, signal width, amplitude and/or burst pattern which are correlated to the degree of inflammation of the specific organ. Accordingly, electrodes positioned along a vagal nerve may be used to sense afferent nerve signals that are received by sensing module 102 and provided to control unit 106 for use in determining an inflammation metric for a specific organ or multiple organs. Various aspects of the afferent vagal nerve signal that may be measured for determining an inflammation metric include amplitude, signal width, frequency, and burst pattern.

In another example, a nerve lead such as lead 40 or a cardiac lead such as leads 20 or 30 may be used to deliver a stimulus pulse to a vagal nerve for measuring an indirect compound action potential. Electrodes along the same lead (or a different lead) are used to sense a compound action potential returning from a targeted organ, i.e. in indirect compound action potential, in response to the stimulation pulse. For example, a bipolar, tri-polar or multi-polar cuff electrode positioned along a vagal nerve may be used to deliver a stimulation pulse using one pair of electrodes and sense a returning compound action potential using the same or a different pair of electrodes. The time interval between the stimulus pulse until the indirect compound action potential component is sensed is measured. An increased time interval compared to an established or previously measured baseline time interval indicating latency of the compound action potential is an indicator of a pro-inflammatory response. Accordingly, the control unit 106 may be configured to measure the latency of an indirect compound action potential component as an inflammation metric in one embodiment.

Monitoring of an inflammation signal may be performed in a substantially continuous or ongoing manner or on a scheduled or periodic basis. In some embodiments, multiple inflammation metrics may be computed using one or more sensed signals. Multiple metrics may be monitored simultaneously or one metric may serve as a primary detection metric and one or more additional metrics may be used to confirm detection of inflammation. For example, if increased atrial fibrillation burden is detected as a primary indicator of an elevated inflammatory response, a measurement of an afferent vagal nerve signal may be measured to confirm the elevated inflammatory response.

An inflammation detection threshold applied to an inflammation metric at block 206 may be defined based on a previously measured baseline of the inflammation metric or based on clinical studies of a patient population. Inflammation detection may be made based on an increasing trend of the inflammation metric (or decreasing trend depending on the metric being used) over a series of consecutive measurements as opposed to a particular threshold crossing in some embodiments.

If inflammation is detected at block 206, vagal stimulation is delivered at block 208 according to the established stimulation parameters as described above. The vagal nerve stimulation may be delivered 24 hours per day or delivered with on and off periods until the inflammation condition is improved. In some embodiments, an alert or notification may be generated upon initiating vagal stimulation and the vagal stimulation may continue until a clinician intervenes. Alternatively, the same metric(s) used to detect inflammation or another metric or combination of metrics may be monitored at block 210 to detect a reduced inflammatory condition. If inflammation metric(s) indicate a reduced inflammatory condition, the vagal stimulation therapy may be stopped (or decreased) at block 212. The process returns to block 204 to continue monitoring an inflammation signal.

In some embodiments, in response to a clinician alert or notification that inflammation has been detected and vagal nerve stimulation therapy started, clinical measurements of the inflammatory condition may be performed. For example, biomarkers of inflammation measured from the blood or urine may be measured at desired intervals after starting the stimulation therapy. The results may be entered into programmer 60 or remote patient database 62 for transmission to IMD 10. In this way, control unit 106 can respond to biomarker measurements collected from the patient during the course of the stimulation therapy. Control unit 106 can respond to an improvement in the inflammation condition detected based on biomarker measurements received by IMD 10 via telemetry by adjusting the stimulation therapy, e.g. by decreasing or turning off vagal nerve stimulation pulse delivery.

Flow chart 200 and other flow charts presented herein are intended to illustrate the functional operation of the IMD, and should not be construed as reflective of a specific form of software or hardware necessary to practice the methods described. It is believed that the particular form of software, firmware and/or hardware will be determined primarily by the particular system architecture employed in the device and by the particular detection and therapy delivery methodologies employed by the device. Providing software, firmware and/or hardware to accomplish the described functionality in the context of any modern IMD, given the disclosure herein, is within the abilities of one of skill in the art.

Methods described in conjunction with flow charts presented herein may be implemented in a non-transitory computer-readable medium that stores instructions for causing a programmable processor to carry out the methods described. A "non-transitory computer-readable medium" includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

Figure 5:
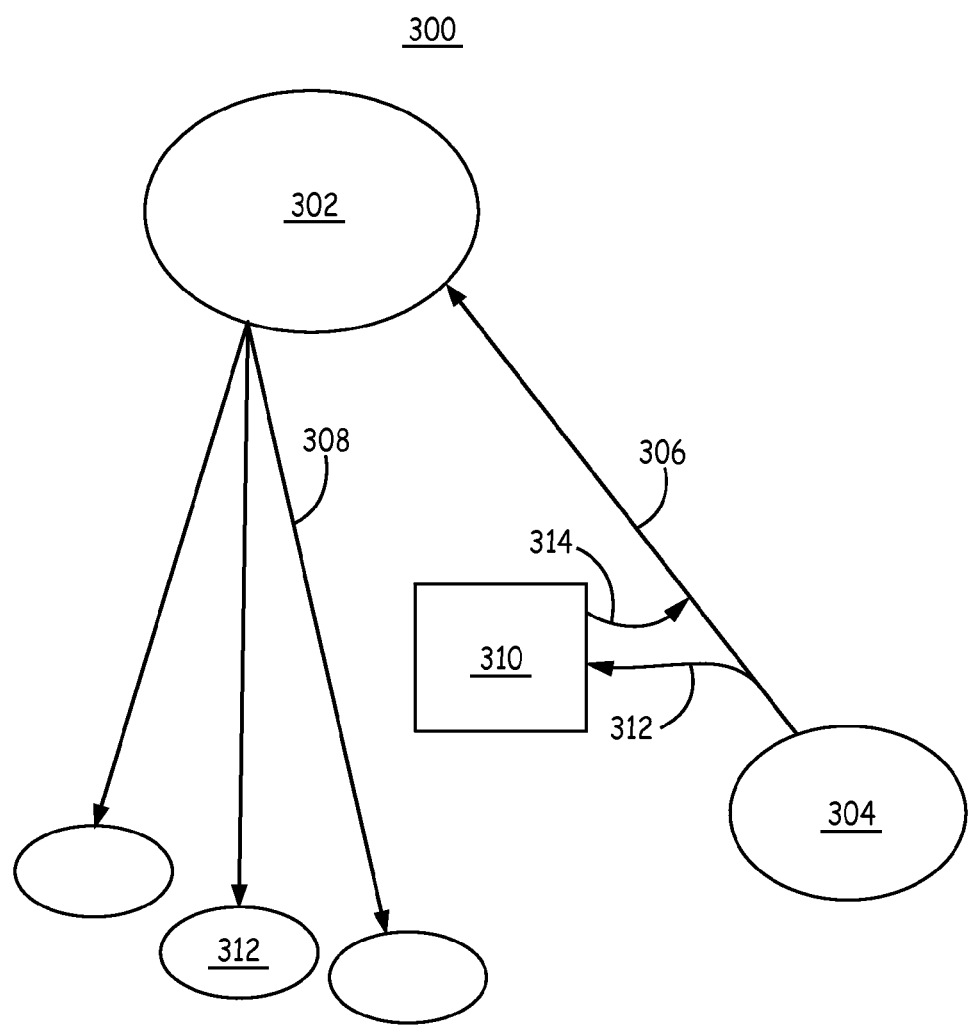
FIG. 5 is a schematic diagram of the technique for modulating vagal nerve signals for controlling inflammation according to an illustrative embodiment.

FIG. 5 is a schematic diagram of the technique for modulating vagal nerve signals for controlling inflammation according to an illustrative embodiment. A vagal nerve branch 306 extends from a subject's brain 302 to an organ 304 innervated by vagal nerve branch 306. IMD 310 senses afferent nerve signals 312 via sensing electrodes operatively positioned relative to vagal nerve branch 306. Aspects of the afferent nerve signal are monitored to detect inflammation, such as signal amplitude, signal width, signal frequency, burst pattern, etc. In particular, an afferent nerve signal having properties corresponding to receptor signals associated with inflammation, such as a chemoreceptor signal or ischemia receptor signal, may be monitored. If afferent nerve signals 312 sensed by IMD 310 indicate organ 304 is being affected by inflammation, IMD 310 delivers electrical stimulation pulse therapy 314 to the afferent nerve fibers of vagal nerve branch 306. The stimulation pulse therapy 314 is controlled by IMD 310 to deliver stimulation pulses corresponding to the organ-specific afferent nerve signals, which may correspond to specific receptor signals associated with sensing inflammation, such as stretch receptor signals, chemoreceptor signals, signals from ischemia receptors or sensors or other receptors of organ 304 producing signals indicating inflammation.

These "simulated inflammatory response" stimulation pulses, are transmitted by nerve branch 306 to brain 302 to trigger brain 302 to provide an anti-inflammatory response to down regulate the inflammation affecting organ 304. The afferent vagal nerve stimulation pulses 314 are not necessarily delivered to the nerve 306 of affected organ 304 as shown in FIG. 5. Afferent nerve stimulation pulses may alternatively or additionally be delivered to another vagal nerve to provide simulated inflammatory response signals to brain 302. In response to the simulated inflammatory response stimulation pulses, the brain 302 will transmit efferent vagal nerve signals along vagal nerve branches 308 to inflammation control centers 312 in the subject's body. The inflammation control centers 306 are expected to respond by producing an anti-inflammatory response, for example by inhibiting synthesis of TNF in the liver, spleen and heart and reducing serum concentrations of TNF.

This induced anti-inflammatory response may provide a greater anti-inflammatory response than that produced without the delivery of the stimulation pulses to the afferent nerve fibers of nerve branch 306. In this way, afferent nerve fiber signal sensing and stimulation can be used to control inflammation affecting a particular organ or organs and diminish or preclude an exacerbated inflammatory condition.

Figure 6:
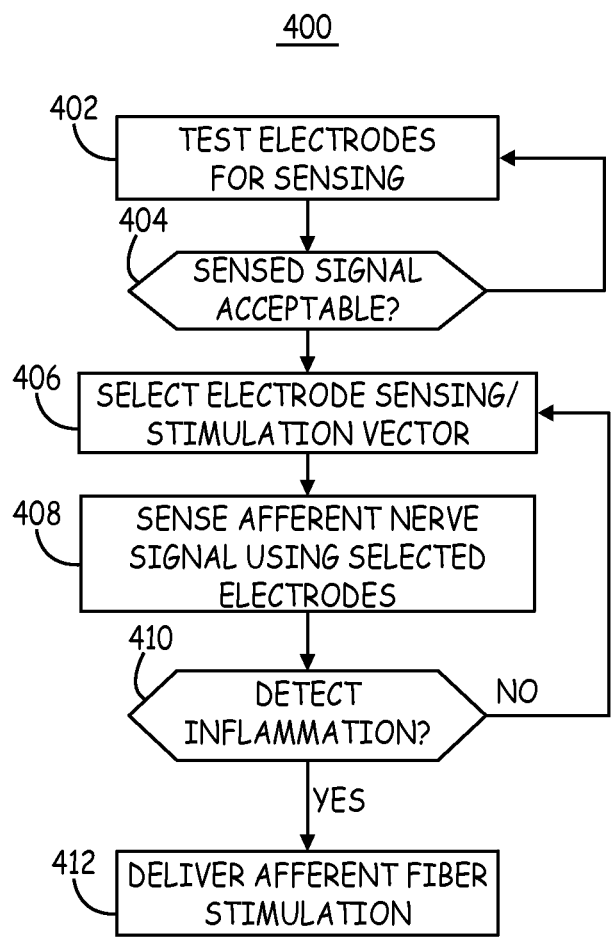
FIG. 6 is a flow chart of a method for detecting and treating an inflammatory condition according to one embodiment.

FIG. 6 is a flow chart of a method 400 for detecting and treating an inflammatory condition according to one embodiment. The method shown in FIG. 6 may be performed using any of the multi-polar cardiac or nerve electrode configurations shown in FIGS. 1, 2A and 2B. At block 402, electrodes are selected by the sensing module to determine which electrode combination enables sensing of nerve signals. The electrodes may be tested to determine which electrodes can be used to successfully deliver a stimulation pulse or pulse train based on successful sensing of an indirect compound action potential signal. Alternatively, electrodes may be selected to sense intrinsic nerve signals without delivering a stimulation pulse to identify an electrode vector nearest an adjacent vagal nerve for optimal sensing/and or stimulation of the nerve.

An electrode vector, which may be a pair or combination of electrodes selected to form a sensing bipole, resulting in an acceptable nerve signal is identified from the available electrodes at block 404. The identified electrode vector is selected for use in sensing a nerve signal and/or stimulating the vagal nerve at block 406. Based on the confirmed sensing of a vagal nerve signal, the selected electrode pair is known to be in operative relation to an adjacent vagal nerve for sensing and/or stimulation of the vagal nerve.

One or more electrode vectors may be identified and selected at blocks 404 and 406. A sensing electrode vector may be identified and selected for sensing nerve signals at a sensing site. A different electrode vector may be identified and selected from the same lead or a different lead for delivering therapeutic electrical stimulation pulses at the same or another site. Afferent nerve fiber stimulation may be delivered along a vagal nerve innervating an affected organ or a different organ. In some embodiments, afferent nerve signals corresponding to receptors sensing inflammation conditions at a particular organ may be sensed along one vagal nerve and stimulation pulses may be delivered to another vagal nerve, associated with the same or a different organ, for artificially increasing the inflammation feedback signals delivered to the brain via the stimulated afferent nerve fiber. As such, electrode selection at blocks 402 through 406 may involve selection of multiple electrode vectors.

At block 408, afferent vagal nerve signals are sensed for use in determining inflammation metric(s) as described previously. The inflammation metric(s) is/are compared to detection criteria at block 410. If inflammation is detected, as determined at block 410, stimulation pulses are delivered to selectively stimulate an afferent nerve fiber to cause an anti-inflammatory response at block 412.

Thus, a medical device system and associated method for modulating vagal signals to reduce inflammation have been presented in the foregoing description with reference to specific embodiments. It is appreciated that various modifications to the referenced embodiments may be made without departing from the scope of the disclosure as set forth in the following claims.

The invention claimed is:

1. A device for controlling an inflammatory condition, comprising:
   a plurality of electrodes for sensing an electrical signal and for delivering electrical stimulation pulses;
   a sensing module for receiving the electrical signal from the plurality of electrodes;
   a pulse generator coupled to the plurality of electrodes for delivering the electrical stimulation pulses to modulate vagal nerve signals; and
   a controller coupled to the sensing module and the pulse generator and configured to:
   determine an inflammation metric from the sensed electrical signal;
   compare the metric to an inflammation detection threshold; and
   control the pulse generator to deliver the electrical stimulation pulses in response to the metric meeting the inflammation detection threshold to modulate the vagal nerve signals to cause an anti-inflammatory response, wherein the plurality of electrodes comprise electrodes positioned along a vagal nerve, the controller further configured to:
   control the pulse generator to deliver a stimulating pulse to the vagal nerve,
   receive an indirect compound action potential signal sensed by the sensing module responsive to the stimulating pulse,
   measure a time interval between the stimulating pulse and the received action potential signal, and
   determine the inflammation metric using the measured time interval.

2. The device of claim 1, wherein the plurality of electrodes comprise cardiac electrodes for sensing a cardiac electrical signal, the controller configured to determine the inflammation metric using the cardiac electrical signal.

3. The device of claim 2, wherein the cardiac electrical signal is a myocardial signal and determining the inflammation metric comprises at least one of detecting atrial fibrillation, determining a ratio of atrial and ventricular rates, determining a heart rate variability and detecting a shift of an S-T segment of the cardiac signal.

4. The device of claim 1, wherein the plurality of electrodes comprise electrodes positioned along a vagal nerve for sensing a nerve signal; the controller configured to determine the inflammation metric from the nerve signal.

5. The device of claim 4, wherein the inflammation metric is determined from an afferent nerve signal having properties corresponding to a specific receptor of an organ innervated by the vagal nerve.

6. The device of claim 1, wherein the plurality of electrodes comprise cardiac electrodes adapted to be positioned along vagal nerve tissue, the electrical stimulation pulses delivered to a vagal nerve via the cardiac electrodes.

7. The device of claim 1, wherein the plurality of electrodes comprise nerve electrodes adapted to be operatively positioned along a vagal nerve, the electrical stimulation pulses delivered to the vagal nerve via the nerve electrodes.

8. The device of claim 1, further comprising a memory storing a set of stimulation parameters for selectively stimulating a vagal nerve fiber, the controller configured to control the pulse generator to deliver the electrical stimulation pulses according to the stored stimulation parameters.

9. The device of claim 8, wherein the stimulation parameters correspond to an intrinsic signal property of an afferent vagal nerve fiber.

10. The device of claim 1, wherein the controller is further configured to detect a decrease in an inflammation condition after delivering the electrical stimulation pulses and control the pulse generator to adjust the delivery of the electrical stimulation pulses in response to the detected decrease.

11. A method for operating a medical device to control an inflammatory condition, comprising:
    receiving an electrical signal from selected ones of a plurality of electrodes electrically coupled to the medical device;
    determining an inflammation metric from the sensed electrical signal;
    comparing the metric to an inflammation detection threshold;
    selectively delivering electrical stimulation pulses in response to the metric meeting the inflammation detection threshold to modulate vagal nerve signals to cause an anti-inflammatory response;
    delivering a stimulating pulse to a vagal nerve,
    receiving a compound action potential signal responsive to the stimulating pulse;
    measuring a time interval between the stimulating pulse and the received action potential signal; and
    determining the inflammation metric using the measured time interval.

12. The method of claim 11, further comprising sensing a cardiac electrical signal from selected ones of the plurality of electrodes, wherein determining the inflammation metric comprises using the cardiac electrical signal.

13. The method of claim 12, wherein sensing the cardiac electrical signal comprises sensing a myocardial signal and determining the inflammation metric comprises one of detecting atrial fibrillation, determining a ratio of atrial and ventricular rates, determining a heart rate variability and detecting a shift of an S-T segment of the cardiac signal.

14. The method of claim 11, further comprising sensing an afferent nerve signal from the selected ones of the plurality of electrodes, wherein the inflammation metric is determined in response to the afferent nerve signal.

15. The method of claim 14, wherein the inflammation metric is determined from an afferent nerve signal having properties corresponding to a specific receptor of an organ innervated by the vagal nerve.

16. The method of claim 11, wherein the plurality of electrodes comprise cardiac electrodes adapted to be positioned along vagal nerve tissue, and further comprising delivering the electrical stimulation pulses to a vagal nerve via the cardiac electrodes.

17. The method of claim 11, wherein the plurality of electrodes comprise nerve electrodes adapted to be positioned along a vagal nerve, and further comprising delivering the electrical stimulation pulses to a vagal nerve via the nerve electrodes.

18. The method of claim 11, further comprising:
    storing in a memory of the medical device a set of stimulation parameters for selectively stimulating a vagal nerve fiber; and
    delivering the electrical stimulation pulses according to the stored stimulation parameters.

19. The method of claim 18, further comprising delivering the electrical stimulation pulses according to a stimulation parameter corresponding to an intrinsic signal property of an afferent vagal nerve fiber.

20. The method of claim 11, further comprising:
    detecting a decrease in an inflammation condition after delivering the electrical stimulation pulses; and
    adjusting the delivery of the electrical stimulation pulses in response to the detected decrease.

21. A non-transitory, computer-readable medium comprising instructions for controlling a medical device to perform a method, the method comprising:
    receiving an electrical signal from selected ones of a plurality of electrodes electrically coupled to the medical device;
    determining an inflammation metric from the sensed electrical signal;
    comparing the metric to an inflammation detection threshold;
    selectively delivering electrical stimulation pulses in response to the metric meeting the inflammation detection threshold to modulate vagal nerve signals to cause an anti-inflammatory response;
    delivering a stimulating pulse to a vagal nerve,
    receiving a compound action potential signal responsive to the stimulating pulse;
    measuring a time interval between the stimulating pulse and the received action potential signal; and
    determining the inflammation metric using the measured time interval.

* * * * *